United States Patent [19]
Singh

[11] Patent Number: 5,871,715
[45] Date of Patent: Feb. 16, 1999

[54] STANNOUS FLUORIDE GEL WITH IMPROVED STAND-UP

[75] Inventor: Pritpal Singh, Newark, Calif.

[73] Assignee: Gillette Canada Inc., Kirkland, Canada

[21] Appl. No.: 808,902

[22] Filed: Feb. 28, 1997

[51] Int. Cl.$^6$ .............................. A61K 7/16; A61K 7/18; A61K 33/16
[52] U.S. Cl. ................. 424/52; 424/49; 424/673
[58] Field of Search ........................ 424/49–88

[56] References Cited

U.S. PATENT DOCUMENTS

| | | | |
|---|---|---|---|
| 2,751,328 | 6/1956 | Sanders | 167/93 |
| 2,839,448 | 6/1958 | Hager et al. | 167/93 |
| 3,070,510 | 12/1962 | Cooley et al. | 167/93 |
| 3,105,013 | 9/1963 | Saul et al. | 167/93 |
| 3,282,792 | 11/1966 | Fiscella | 167/93 |
| 3,337,412 | 8/1967 | Elbreder | 167/93 |
| 3,689,637 | 9/1972 | Pader | 424/52 |
| 3,892,843 | 7/1975 | Muhler et al. | 424/52 |
| 3,929,988 | 12/1975 | Barth | 424/54 |
| 3,939,261 | 2/1976 | Barth | 424/49 |
| 3,957,964 | 5/1976 | Grimm | 424/10 |
| 4,022,881 | 5/1977 | Hawking | 424/52 |
| 4,071,615 | 1/1978 | Barth | 424/52 |
| 4,132,771 | 1/1979 | Schreiber et al. | 424/52 |
| 4,170,635 | 10/1979 | Barth | 424/79 |
| 4,203,966 | 5/1980 | Faunce | 424/52 |
| 4,251,507 | 2/1981 | Olson | 424/49 |
| 4,267,167 | 5/1981 | Weitzman | 424/52 |
| 4,357,313 | 11/1982 | Harvey et al. | 424/49 |
| 4,396,599 | 8/1983 | Sipos | 424/52 |
| 4,418,057 | 11/1983 | Groat et al. | 424/151 |
| 4,533,544 | 8/1985 | Groat et al. | 424/52 |
| 4,568,540 | 2/1986 | Asano et al. | 424/52 |
| 4,582,701 | 4/1986 | Piechota | 424/52 |
| 4,647,451 | 3/1987 | Piechota et al. | 424/52 |
| 4,837,008 | 6/1989 | Rudy et al. | 424/53 |
| 5,360,615 | 11/1994 | Yu et al. | 424/455 |
| 5,614,175 | 3/1997 | Winston et al. | 424/52 |
| 5,674,474 | 10/1997 | Fisher et al. | 424/52 |

FOREIGN PATENT DOCUMENTS

| | | | |
|---|---|---|---|
| 2 216 005 | 10/1989 | United Kingdom | A61K 7/24 |
| WO 95/28911 | 11/1995 | WIPO | A61K 7/18 |

OTHER PUBLICATIONS

Federal Register/ vol. 60, No. 194 / Friday Oct. 6, 1995 / Rules an d Regulations pp. 52474–52510.
Aerosil Fumed Silica, Degussa pp. 1–32.
Natrosol Hydroxyethylcellulose A Nonionic Water–Soluble Polymer, Physical and Chemical Properties Aqualon. 1994 pp. 1–20.

*Primary Examiner*—Shep K. Rose
*Attorney, Agent, or Firm*—Chester Cekala

[57] ABSTRACT

The present invention relates to a stannous fluoride-containing gel comprising from about 0.3% to about 1.0% (by weight) stannous fluoride, from about 1.0% to about 10% (by weight) silica thickening agent and anhydrous glycerin. Preferably, these gels also contain from about 0.01% to about 5% (by weight) of a gum system, e.g. hydroxyethyl cellulose. These gels exhibit very good ribbon stand-up qualities and excellent fluoride ion and stannous ion stability. Also, the present invention relates to an improved method for producing the above gels. This method uses mixing equipment commonly employed to manufacture dentifrices and provides a simplified processing scheme.

8 Claims, No Drawings

STANNOUS FLUORIDE GEL WITH IMPROVED STAND-UP

BACKGROUND OF THE INVENTION

1. Field of the Invention

This invention relates to a dental gel containing stannous fluoride and more particularly to a process for producing a stannous fluoride gel having improved ribbon or stand-up characteristics when dispensed from a tube. These gels exhibit surprisingly good stannous ion and fluoride ion stability.

2. The Prior Art

Stannous fluoride ($SnF_2$) has been reported to be an effective agent for treating various oral conditions. The most important dental benefit imparted by stannous fluoride is the reduction of dental caries. Stannous fluoride-containing over-the-counter dentifrices have been classified by the U.S. Food & Drug Administration as therapeutic agents that provide protection against the development of dental caries. Early stannous fluoride dentifrices contained abrasive systems that reacted with fluoride making these products ineffective in reducing tooth decay. Significant progress in the development of new abrasives has led to the development of stannous fluoride dentifrices with significantly improved fluoride ion availability. However, the antibacterial stannous ion undergoes rapid hydrolysis and oxidation in aqueous based dentifrice's resulting in essentially no available stannous ion.

Self applied topical fluoride products now exist based on 0.4% stannous fluoride but without formula excipients that interact with fluoride and stannous ions (e.g., abrasives, water, surfactants, etc.). The principal excipient of these stannous fluoride "gels" is the humectant glycerin. The prior art clearly shows the method of manufacture (e.g, mixing times, temperature, manufacturing equipment) is critical to ensure stability and availability of the fluoride and stannous ion. Indeed the process outlined in U.S. Pat. Nos. 4,418,057 and 4,533,544 for a stannous fluoride gel presents numerous challenges for the manufacturing team. It requires the preparation of several side phases consisting of precise levels of stannous fluoride and glycerin. Mixing temperatures can range up to 180° C. which is not easily achieved in most plants without special equipment. Another draw back to the gel preparations described in U.S. Pat. Nos. 4,418,057 and 4,533,544 is that the gels have a semi-liquid consistency, and when dispensed on the bristles of a toothbrush, the gel immediately sinks through the bristles and runs off the brush so that only a relatively small portion of the dispensed product is retained on the toothbrush. Consequently, $SnF_2$ suspended in the thickened anhydrous glycerin has not found wide acceptability as a home-care product due to the face that the semi-fluid gel composition can not be controllably retained on toothbrush bristles and then applied to teeth to reliably supply $SnF_2$ for the treatment of dental carry.

It is therefore an object to the present invention to provide a processing scheme for producing a stannous fluoride gel which avoids the shortcomings of the prior art.

It is also an object of the present invention to provide a stannous fluoride gel with good ribbon stand-up qualities and surprisingly good stannous ion and fluoride ion stability.

These and other objects will be made clear from the following:

SUMMARY OF THE INVENTION

The present invention relates to a stannous fluoride-containing gel comprising from about 0.3% to about 1.0% (by weight) stannous fluoride, from about 1.0% to about 10% (by weight) silica thickening agent and an anhydrous base. Preferably, these gels also contain from about 0.01% to about 5% (by weight) of a gum system, e.g. hydroxyethyl cellulose.

These gels exhibit very good ribbon stand-up qualities and excellent fluoride ion and stannous ion stability.

Also, the present invention relates to an improved method for producing the above gels. This method uses mixing equipment commonly employed to manufacture dentifrices and provides a simplified processing scheme. This method involves (a) dissolving about 0.01 to about 5.0 parts gum system in an anhydrous base; (b) blending in from about 1 to about 10 parts silica thickening agent; and (c) adding from about 0.36 to about 0.46 parts stannous fluoride, wherein said anhydrous base in present in sufficient quantity such that the sum of all ingredient parts is 100.

The present inventive improvement in gel stand-up, stannous/fluoride ion stability and processing techniques is predicated on the incorporation in the gel of a silica thickening agent.

DESCRIPTION OF THE PREFERRED EMBODIMENTS

All percentages and ratios used herein are on a weight basis unless otherwise specified.

As used herein ribbon "stand-up" qualities relates to a gel ribbon which has an extrudable consistency such that the extruded ribbon of the gel, when dispensed on to the bristles of a toothbrush, will stand up on the top surface of the bristles for a time sufficient to allow full application of the gel to the teeth, e.g., time interval of least 0.5 to 1.0 minutes. Stannous fluoride-containing gel compositions of the present invention are generally comprised of from about 0.3% to about 1.0% (preferably 0.36% to about 0.46%) stannous fluoride, from about 1.0% to about 10.0% (preferably 3.0% to 8.0%) silica thickening agent and an anhydrous base. Preferably the anhydrous base is glycerin. Furthermore, preferred gels of the present invention also include from about 0.1% to about 5% of a gum system most preferably from about 0.3% to about 1.0% of a gum system.

Thickening silica is used for three reasons. First, it increases the batch viscosity during processing ensuring good dispersion of the stannous fluoride (i.e., it prevents the stannous fluoride from settling to the bottom of the tank). Second, it provides a ribbon with very good stand-up characteristics. Third, I have observed that the resulting gel product exhibits surprisingly good stannous ion and fluoride ion stability. The thickening silica used in the practice of the present invention is a colloidal or fumed silica. These silicas are in the form of finely divided particles, typically having a particle size less than about 4 microns. Fumed silica is typically made by combustion of silicon tetrachloride in hydrogen-oxygen furnaces. Fumed silica is commercially available under the trade name Aerosil from Degussa Corporation and under the trade name Cab-O-Sil from Cabot Corporation. A preferred fumed silica is Aerosil 200 from Degussa Corporation, Ridgefield Park, N.J. As described in the manufactures literature (Brochure PT 6-50-1-694H), Aerosil 200 has the following properties:

| | |
|---|---|
| •BET surface area (D1N 66131) | 200 ± 25 $m^2/g$ |
| •Average particle size | 12 nm |
| •Standard tamped density (D1N ISO 787/X1, J1S K 5101/18) | approx. 40 g/l |
| •Moisture (D1N ISO 787/11, ASTM D 280, J1S K 5101/21) | <1.5 |
| •pH (in 4% aqueous dispersion) | 3.6–4.3 |

-continued

| •SiO$_2$ (based on material ignited for 2 hours at 1000° C.) | >99.8% |

A gum system may optionally be included in the SnF$_2$ gels of the present invention at a concentration of from about 0.01% to about 5.0% by weight preferably from about 0.3% to abut 1.0% by weight. The gum systems used in the practice of the present invention are food grade gums. Suitable gums are selected from the group consisting of: hydroxyethylcellulose;

A preferred hydroxyethylcellulose is Natrosol® 250 brand hydroxyethylcellulose manufactured by Aqualon Division of Hercules Inc., Wilmington, Del. Food grade, "LR" type hydroxyethylcellulose is the most preferred. Preferred hydroxyethylcellulose has a molecular weight of about $9.0\times10^4$ as estimate from intrinsic viscosity measurements as provided by the manufacturer. Preferred hydroxyethylcellulose has a low moisture content on a particle size such that at least 90% passes through a U.S. No. 40 mesh.

Compositions of the present invention may also contain an effective amount of a flavor component which does not interfere with the stability of the stannous ions and fluoride ions. The flavor ingredient typically constitutes from about 0.05% to about 2.0% (preferably from about 0.1 to about 1.5%) of the gel composition. Suitable flavoring constituents are flavoring oils, e.g. oils of spearmint, peppermint, wintergreen, clove, methyl salicylate, cinaminic aldehydes and menthol.

Compositions of the present invention may also contain other typical toothpastes and gel additives provided that they do not interfere with the stability of the stannous ions and fluoride ions in the gel. These compositions are free of abrasives.

Gel compositions of the present invention are prepared by (a) dissolving about 0.01 to about 5.0 parts gum system in an anhydrous base; (b) blending in from about 1 to about 10 parts silica thickening agent; and (c) adding from about 0.36 to about 0.46 parts stannous fluoride, wherein said anhydrous base in present in sufficient quantity such that the sum of all ingredient parts is 100.

Preferably, the gum system is hydroxyethyl cellulose, the anhydrous base is glycerin (99.5%) and the silica thickening agent is fumed silica. Also, step (a) is conducted at a temperature above 120° C., typically about 150° C. Optionally, the manufacturing method also includes an additional flavor addition step (d) which involves mixing from about 0.05 to about 2.0 parts of a flavor component that does not interfere with the stability of stannous ions or fluoride ions in the resulting composition. Preferably, the composition is cooled to a temperature below 40° C. prior to step (d). The most preferred method utilizes from about 0.1 parts to about 2.0 parts hydroxyethyl cellulose, from about 3 to about 8 parts formed silica and from about 0.1 to about 1.5 parts flavor.

The following examples are further illustrative of the present invention, but it is understood that the invention is not limited thereto.

EXAMPLE

Briefly the following method to produce a batch of stabilized stannous fluoride gel uses mixing equipment commonly employed to manufacture dentifrices. The main batch tank is a Nauta mixer. Also required is a small side phase tank equipped with an immersion heater and overhead Cowles blade. The following procedure was used to prepare the gel described in Table 1:

I. Preparation of Gum Phase (Phase A):

Add most of the formula amount of Phase glycerin (99.5%) (See Sno. 010 on formula table below) into the side phase tank equipped with an immersion heater and an overhead mixer with Cowles blade.

Start mixing. Adjust the height and speed of mixer to obtain a good vortex.

Slowly add formula amount of hydroxylethylcellulose (Sno.020) into the vortex. Continue mixing until well dispersed.

Initiate heating and heat the phase to a minimum of 130° C. Continue mixing while heating, adjusting the speed of the mixer to avoid splashing, as the phase becomes less viscous on heating.

Turn off the heater when the batch temperature reaches 130° C. and continue mixing for 15 minutes.

Stop mixing and evaluate the batch for the presence of gum particles. If the particles are seen, mix for an additional 15 minutes, or until these are dispersed.

Add remaining amount of glycerin (Sno.030) into the batch and continue mixing and start cooling with the water jacket until the batch temperature drops below 45° C.

Continue agitating the solution at low speed until the phase is transferred into the main batch tank.

II. Preparation of Main Phase (Phase B):

Transfer the gum phase (Phase A) into the Nauta mixer

Turn on the lump breakers, start sweep with the auger in the down position Weigh out the remaining formula amount of glycerin (Sno.040) into the side phase kettle and transfer into the Nauta mixer, thereby rinsing the phase tank and hoses.

Turn off the lump breakers. Close and seal the nauta tank and adjust vacuum to 26" Hg. Turn off vacuum.

Using the feed port, slowly draw in the formula amount of Aerosil 200 brand fumed Silica (Sno.050).

Stop addition when the vacuum drops to 15" Hg. Continue mixing under closed vacuum until all of the Aerosil is blended into the batch.

Restore vacuum to 26" Hg and then close off vacuum. Repeat previous steps until all of the Aerosil has been blended into the batch.

Start cooling. Continue cooling during subsequent steps until the temperature of the batch is below 40° C.

Start vacuum and mix under open vacuum for 15 minutes.

Release vacuum and open the top manhole of the mixer. Park the sweep close to the manhole. Switch auger on and in the down position. Start the lumpbreakers.

Slowly add the formula amount of stannous fluoride (Sno.060).

Close and seal the mixer. Start the sweep and mix under open vacuum for 10 minutes.

Release vacuum and stop lumpbreakers. Recirculate the batch by removing four pails of the batch from the bottom port and adding it to the top of the tank.

Mix under open vacuum for 5 minutes.

Close vacuum.

III. Completion of Batch

Continue mixing and cooling until batch temperature is below 40° C.

Draw in the formula amount of flavor (Sno.070). Mix under closed vacuum for 5 minutes.

Mix under open vacuum for 10 minutes

Stop mixing. Release vacuum and open top cover of the mixer.

The resulting product exhibits exceptional smoothness, clarity and is free from entrapped air.

| Part/Phase | Sno. | Ingredients | % w/w | Amount (Kg.) |
|---|---|---|---|---|
| A. | 010 | Glycerin 99.5% | 35.0000 | 350.000 |
|  | 020 | Hydroxyethyl Cellulose 250 (L) (Natrosol 250 L) | 0.4500 | 4.500 |
|  | 030 | Glycerin 99.5% | 40.0000 | 400.000 |
| B. | 040 | Glycerin 99.5% | 18.6100 | 186.100 |
|  | 050 | Aerosil 200 | 4.5000 | 45.000 |
|  | 060 | Stannous Fluoride | 0.4400 | 4.400 |
|  | 070 | Flavor TP 4940 | 1.0000 | 10.000 |
|  |  | TOTAL | 100.0000 | 1000.000 |

The accelerated stability of batches prepared using the above method has been evaluated. Available Stannous and Fluoride ion concentrations in weight percentages were determined via the USP methods. Data is shown below—

| Analyzed for | Zero Time RT | 4 weeks at the following conditions | | | | 8 weeks at the following conditions | | | | 12 weeks at the following conditions | | | |
|---|---|---|---|---|---|---|---|---|---|---|---|---|---|
| | | 50° C. | 40° C. | RT | 4° C. | 50° C. | 40° C. | RT | 4° C. | 50° C. | 40° C. | RT | 4° C. |
| Stannous Ion | 0.432, 0.428 | 0.398, 0.399 | 0.405, 0.403 | 0.416, 0.418 | 0.408, 0.425 | 0.391, 0.401 | 0.394, 0.391 | 0.407, 0.385 | 0.408, 0.399 | 0.405, 0.410 | 0.409, 0.402 | 0.411, 0.416 | 0.424, 0.425 |
| Fluoride Ion | 0.445, 0.460 | 0.412, 0.427 | 0.414, 0.407 | 0.427, 0.439 | 0.427, 0.442 | 0.392, 0.397 | 0.407, 0.417 | 0.423, 0.431 | 0.445, 0.439 | 0.357, 0.355 | 0.373, 0.364 | 0.374, 0.339 | 0.324, 0.339 |

Note: "RT" = Room Temperature

What is claimed is:

1. An abrasive-free stannous fluoride gel composition exhibiting improved stand-up and good stannous ion and fluoride ion stability formulated from ingredients consisting essentially of about 0.3% to about 1.0% by weight stannous fluoride, and about 1.0% to about 10.0% fumed silica and anhydrous glycerin, wherein the resulting gel provides an effective therapeutic amount of stannous ions and fluoride ions.

2. The composition of claim 1 containing from about 3.0% to about 8% fumed silica.

3. The composition of claim 2 further comprising a gum system.

4. The composition of claim 3 wherein said gum system is selected from the group consisting of hydroxyethylcellulose, xanthan gum and carageenan.

5. The composition of claim 4 wherein said gum system is hydroxyethyl cellulose.

6. The composition of claim 5 wherein the gum system is present in the composition at a concentration of about 0.01 to about 5.00% by weight.

7. The composition of claim 6 further comprising from about 0.05% to about 2.0% of a flavor component which does not significantly destabilize said stannous ion and said fluoride ions.

8. The composition of claim 7 containing from about 0.1% to 1.5% flavor component.

* * * * *